US010711318B2

(12) United States Patent
Lovley et al.

(10) Patent No.: US 10,711,318 B2
(45) Date of Patent: Jul. 14, 2020

(54) MICROBIAL STRAIN FOR ELECTROSYNTHESIS AND ELECTROFERMENTATION

(71) Applicant: University of Massachusetts, Boston, MA (US)

(72) Inventors: Derek R. Lovley, Amherst, MA (US); Toshiyuki Ueki, Amherst, MA (US); Kelly N. Lovley, Amherst, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 59 days.

(21) Appl. No.: 16/194,923

(22) Filed: Nov. 19, 2018

(65) Prior Publication Data

US 2019/0153553 A1 May 23, 2019

Related U.S. Application Data

(60) Provisional application No. 62/588,674, filed on Nov. 20, 2017.

(51) Int. Cl.
*C12M 1/42* (2006.01)
*C12P 5/00* (2006.01)
*C12P 7/40* (2006.01)
*C12N 9/10* (2006.01)
*C12N 9/04* (2006.01)
*C12M 1/00* (2006.01)
*C12P 7/06* (2006.01)
*C12R 1/01* (2006.01)

(52) U.S. Cl.
CPC .............. *C12R 1/01* (2013.01); *C12M 21/12* (2013.01); *C12M 29/04* (2013.01); *C12M 35/02* (2013.01); *C12N 9/0006* (2013.01); *C12N 9/1025* (2013.01); *C12P 5/00* (2013.01); *C12P 7/065* (2013.01); *C12P 7/40* (2013.01)

(58) Field of Classification Search
None
See application file for complete search history.

(56) References Cited

PUBLICATIONS

Thrash et al., "Review: Direct and Indirect Electrical Stimulation of Microbial Metabolism," Environmental Science & Technology, vol. 42, No. 11, 2008, p. 3921-3931.
Lovley,"Powering microbes with electricity: direct electron transfer from electrodes to microbes," Environmental Microbiology Reports (2011) 3(1), 27-35.
Lovley et al., "Electrobiocommodities: powering microbial production of fuels and commodity chemicals from carbon dioxide with electricity," Elsevier, Current Opinion in Biotechnology 2013, 24:385-390.
Tremblay et al.,"Electrifying microbes for the production of chemicals," Frontiers in Microbiology, Mar. 2015, vol. 6, Article 201.

May et al.,"The bioelectrosynthesis of acetate," Elsevier, Current Opinion in Biotechnology, 2016, 42:225-233.
Tremblay et al., "Extracellular Electron Uptake: Among Autotrophs and Mediated by Surfaces," Trends in Biotechnology, Apr. 2017, vol. 35, No. 4, 360-371.
Blanchet et al., "Importance of the hydrogen route in up-scaling electrosynthesis for microbial CO2 reduction," Energy Environ. Sci., 2015, 8, 3731.
Butler et al., "How to Sustainably Feed a Microbe: Strategies for Biological Production of Carbon-Based Commodities with Renewable Electricity," Frontiers in Microbiology, Nov. 2016,vol. 7, Article1879.
Schlegel et al., "Growth of 'Knallgas' Bacteria (Hydrogenomonas) using Direct Electrolysis of the Culture Medium," Nature, Jan. 16, 1965, vol. 205, 308-309.
Kuroda et al., "CO2 Reduction to Methane and Acetate Using a Bio-Electro Reactor With Immobilized Methanogens and Homoacetogens on Electrodes," Energy Conyers. Mgmt. vol. 36, No. 6-9, p. 787-790, 1995.
Nevin et al., "Microbial Electrosynthesis: Feeding Microbes Electricity to Convert Carbon Dioxide and Water to Multicarbon Extracellular Organic Compounds," mBio, May/Jun. 2010, vol. 1, Issue 2 e00103-10.
Strycharz-Glaven et al., "Electrochemical Investigation of a Microbial Solar Cell Reveals a Nonphotosynthetic Biocathode Catalyst," Applied and Environmental Microbiology, Jul. 2013 ,vol. 79, No. 13, p. 3933-3942.
Leary et al., "Metaproteomic evidence of changes in protein expression following a change in electrode potential in a robust biocathode microbiome," Proteomics 2015, 15, 3486-3496.
Yates et al., "Toward understanding long-distance extracellular electron transport in an electroautotrophic microbial community," Energy Environ. Sci.,2016, 9, 3544.
Eddie et al., Metatranscriptomics Supports the Mechanism for Biocathode Electroautotrophy by "Candidatus Tenderia electrophaga," American Society for Microbiology, Mar./Apr. 2017 vol. 2 Issue 2 e00002-17.
Gregory et al,"Graphite electrodes as electron donors for anaerobic respiration," Environmental Microbiology (2004) 6(6), 596-604.
Ross et al.,"Towards Electrosynthesis in Shewanella: Energetics of Reversing the Mtr Pathway for Reductive Metabolism," PLos One, Feb. 2011, vol. 6 , Issue 2 , e16649.
Nevin et al.,"Electrosynthesis of Organic Compounds from Carbon Dioxide is Catalyzed by a Diversity of Acetogenic Microorganisms," Applied and Environmental Microbiology, May 2011, p. 2882-2886, vol. 77, No. 9.
Lovley et al.,"Geobacter: The Microbe Electric's Physiology, Ecology, and Practical Applications," Advances in Microbial Physiology, vol. 59, Elsevier.
Mahadevan et al.,"In situ to in silico and back: elucidating the physiology and ecology of Geobacter spp. using genome-scale modelling," Nature Reviews, Microbiology, vol. 9, Jan. 2011, p. 39-50.

(Continued)

*Primary Examiner* — Suzanne M Noakes
*Assistant Examiner* — Jae W Lee
(74) *Attorney, Agent, or Firm* — Renner, Otto, Boisselle & Sklar, LLP (57) ABSTRACT

A genetically engineered strain of *Geobacter sulfurreducens* exhibits improved function as a cathode biofilm compared to the wild type strain. The genetically engineered *Geobacter sulfurreducens* strain is capable of using carbon dioxide as a carbon source and electrical current as an energy source for producing a carbonaceous chemical using a reverse tricarboxylic acid pathway.

12 Claims, 5 Drawing Sheets

(56) References Cited

PUBLICATIONS

Lovley, "Syntrophy Goes Electric: Direct Interspecies Electron Transfer," Annual Review of Microbiology. 2017. 71:643-64.
Nevin et al.,"Power output and columbic efficiencies from biofilms of Geobacter sulfurreducens comparable to mixed community microbial fuel cells," Environmental Microbiology (2008) 10(10), 2505-2514.
Yi et al., "Selection of a variant of Geobacter sulfurreducens with enhanced capacity for current production in microbial fuel cells," Elsevier, Biosensors and Bioelectronics 24 (2009) 3498-3503.
Malvankar et al.,"Tunable metallic-like conductivity in microbial nanowire networks," Nature Nanotechnology, vol. 6, Sep. 2011,p. 573-579.
Malvankar et al.,"Biofilm conductivity is a decisive variable for high-current-density Geobacter sulfurreducens microbial fuel cells," Energy Environ. Sci., 2012, 5, 5790.
Yates et al.,"Measuring conductivity of living Geobacter sulfurreducens biofilms," Nature Nanotechnology, vol. 11, Nov. 2016, p. 910-913.
Reply to "Measuring conductivity of living Geobacter sulfurreducens biofilms," Nature Nanotechnology, vol. 11, Nov. 2016, p. 913-914.
Lovley, "Electromicrobiology," Annu. Rev. Microbiol. 2012. 66:391-409.
Robuschi et al.,"Proving Geobacter biofilm connectivity with confocal Raman microscopy," Elsevier, Journal of Electroanalytical Chemistry 793 (2017) 99-103.
Strycharz et al.,"Gene expression and deletion analysis of mechanisms for electron transfer from electrodes to Geobacter sulfurreducens," Elsevier, Bioelectrochemistry 80 (2011) 142-150.
Mahadevan et al.,"Characterization of Metabolism in the Fe(III)-Reducing Organism Geobacter sulfurreducens by Constraint-Based Modeling," Applied and Environmental Microbiology, Feb. 2006, p. 1558-1568.
Feist et al., "Constraint-Based Modeling of Carbon Fixation and the Energetics of Electron Transfer in Geobacter metallireducens," PLoS Comput Biol 10(4): 0003575.
Kanao et al.,"ATP-citrate lyase from the green sulfur bacterium Chlorobium limicola is a heteromeric enzyme composed of two distinct gene products," Eur. J. Biochem. 268, 1670-1678 (2001).
Ueki et al.,"Toward establishing minimum requirements for extracellular electron transfer in Geobacter sulfurreducens," FEMS Microbiology Letters, 2017, vol. 364, No. 9.
Coppi et al,"Identification of an Uptake Hydrogenase Required for Hydrogen-Dependent Reduction of Fe(III) and Other Electron Acceptors by Geobacter sulfurreducens," Journal of Bacteriology, May 2004, p. 3022-3028., vol. 186, No. 10.
Reguera et al.,"Biofilm and Nanowire Production Leads to Increased Current in Geobacter sulfurreducens Fuel Cells," Applied and Environmental Microbiology, Nov. 2006, p. 7345-7348 vol. 72, No. 11.
Nevin et al.,"Anode Biofilm Transcriptomics Reveals Outer Surface Components Essential for High Density Current Production in Geobacter sulfurreducens Fuel Cells," PLOS One, May 2009, vol. 4, Issue 5, e5628.
Schievano et al., "Electro-Fermentation—Merging Electrochemistry with Fermentation in Industrial Applications," Trends in Biotechnology, Nov. 2016, vol. 34, No. 11, p. 866-878.
Coppi et al,"Development of a Genetic System for Geobacter sulfurreducens," Applied and Environmental Microbiology, Jul. 2001, p. 3180-3187, vol. 67, No. 7.
Chan et al.,"Scarless Genome Editing and Stable Inducible Expression Vectors for Geobacter sulfurreducens," Applied and Environmental Microbiology, Oct. 2015,vol. 81, No. 20, p. 7178-7186.
Ueki et al.,"Genetic switches and related tools for controlling gene expression and electrical outputs of Geobacter sulfurreducens," J Ind Microbiol Biotechnol (2016) 43:1561-1575.
Lovley et al., "Rapid Assay for Microbially Reducible Ferric Iron in Aquatic Sediments," Applied and Environmental Microbiology, Jul. 1987, p. 1536-1540 vol. 53, No. 7.
Vargas et al.,"Aromatic Amino Acids Required for Pili Conductivity and Long-Range Extracellular Electron Transport in Geobacter sulfurreducens," mBio Mar./Apr. 2013 vol. 4, Issue 2, :e00105-13.

MICROBIAL STRAIN FOR ELECTROSYNTHESIS AND ELECTROFERMENTATION

This application claims priority to U.S. Provisional Application 62/588,674 filed Nov. 20, 2017, the entire contents of which are incorporated by reference herein.

STATEMENT REGARDING FEDERALLY SPONSORED RESEARCH

Research carried out in connection with this invention was supported in part by the Office of Naval Research grant N000141310549. The United States government may have certain rights in the invention.

TECHNICAL FIELD

The invention relates to systems and methods for generating organic compounds using carbon dioxide as a source of carbon and electrical current as an energy source. More particularly, the invention relates to a genetically engineered strain of *Geobacter sulfurreducens* having improved function as a cathode biofilm.

BACKGROUND

The economics of powering microbial metabolism with electrons derived from cathodes is rapidly improving as the cost of renewable sources of electricity declines. Many proof-of-concept studies have demonstrated the potential for microorganisms to convert carbon dioxide or waste streams into organic commodities with electrons derived from cathodes. However, the rates of electron transfer from cathodes into biofilms have been more than an order of magnitude lower than the rates of electron transfer in the reverse direction when biofilms produce electric current on anodes.

As the availability of renewable sources of electricity rises, feeding microorganisms electrons with an electrode is becoming an increasingly attractive possibility for the production of biofuels and other organic commodities, as well as for bioremediation of organic and metal contamination.

In many studies, $H_2$ produced at the cathode functions as an electron shuttle between the cathode and microbes. Supplying $H_2$ to microorganisms in this manner is a relatively old technology. There are well-developed models for the growth and metabolism of diverse anaerobes with $H_2$ as the electron donor.

Less explored is the possibility of developing biofilms that directly accept electrons from cathodes. Direct electron transfer has several potential benefits over the production of $H_2$, such as lower energy inputs, higher recovery of electrons in products, and the retention of the microbial catalyst as a biofilm. However, without a genetically tractable model microbial system that effectively grows on cathodes there has been no knowledge base of first principles to guide the design of cathode microbial catalysts.

Insights into electron transfer within cathode biofilms have recently been obtained through omics and electrochemical characterization of a multi-species oxygen-reducing biofilm enrichment known as the *Marinobacter*-Chromatiaceae-*Labrenzia* (MCL) biocathode. However, none of the microorganisms in the MCL biofilm has been recovered in pure culture, which has prevented definitive genetic and biochemical investigations into hypothesized electron transport mechanisms. Genetically tractable isolates are also required for the introduction of synthetic pathways to produce high value products. High recovery of electrons in such products is only possible under anaerobic conditions. Anaerobes that are genetically tractable and are also thought to directly accept electrons from cathodes include *Geobacter sulfurreducens*, *G. metallireducens*, *Shewanella oneidensis*, and *Clostridium ljungdahlii*. None of these microorganisms grows well on cathodes.

SUMMARY

Feeding electrons to microorganisms growing on cathodes is a promising sustainable approach to produce fuels and for bioremediation, but poor growth of cathode biofilms has stymied development of these technologies. As described herein, a strain of *Geobacter sulfurreducens*, designated strain ACL, which grows as thick (ca. 35 µm) confluent biofilms on cathodes poised at −500 mV (versus Ag/AgCl) with fumarate as the electron acceptor has been developed. Sustained maximum current consumption rates are $\geq 0.8$ $A/m^2$, which is at least ten-fold higher than the current consumption previously achieved with the wild-type strain. The improved function on the cathode was achieved by introducing genes for an ATP-dependent citrate lyase, completing the complement of enzymes needed for a reverse TCA cycle for the synthesis of biosynthetic precursors from carbon dioxide. Strain ACL provides an important model organism for elucidating the mechanisms for effective anaerobic growth on cathodes and offers unique possibilities as a chassis for the introduction of synthetic pathways to generate high value products with microbial electrosynthesis and electrofermentation.

In one aspect of the invention there is provided a genetically engineered *Geobacter sulfurreducens* strain, wherein the strain contains a genetically engineered modification resulting from the insertion of a genetic element encoding ATP-citrate lyase.

In one embodiment, the genetically engineered *Geobacter sulfurreducens* is capable of effectively growing on a cathode under anaerobic conditions with electrons derived solely from the cathode as electron donor source.

In one embodiment, the genetic element inserted as the modification includes the genes aclA and aclB.

In one embodiment, the genetic element is inserted adjacent the gene GSU1106 of the parent *Geobacter sulfurreducens*.

In one embodiment, the genetically engineered modification further includes the insertion of a gene that encodes bifunctional aldehyde/alcohol dehydrogenase. In one embodiment, the gene encoding bifunctional aldehyde/alcohol dehydrogenase is adhE1.

In one embodiment, the genetically engineered *Geobacter sulfurreducens* strain is configured for producing a carbonaceous chemical containing at least two carbon atoms in a reverse tricarboxylic acid (TCA) pathway.

In one embodiment, the genetically engineered *Geobacter sulfurreducens* strain exhibits improved function as a cathode biofilm compared to the wild-type *Geobacter sulfurreducens* under the same conditions.

In another aspect of the invention there is provided a method of generating a carbonaceous chemical wherein carbon dioxide is a source of carbon. The method includes the steps of: (a) providing a reaction vessel having an anode electrode and a cathode electrode disposed therein, the anode electrode having at least one surface and an anode electrical contact terminal, the cathode electrode having at least one surface and a cathode electrical contact terminal, the cathode electrode having a film of biologically active material comprising the genetically engineered *Geobacter sulfurreducens* strain adjacent the at least one surface of the cathode electrode and in electrical communication therewith, the reaction vessel configured to contain a working fluid having mobile ions therein; (b) providing a reaction medium in contact with the cathode electrode and the anode electrode, the reaction medium containing a substance configured to be oxidized; (c) providing a source of electrical energy electrically connected to the cathode electrical contact terminal and to the anode electrical contact terminal; (d) providing a source of carbon dioxide configured to provide carbon dioxide to the film of biologically active material adjacent the at least one surface of the cathode electrode by way of the reaction medium; (e) operating the source of electrical power to provide electrons to the cathode and to extract electrons from the anode; and (f) generating a carbonaceous chemical containing at least two carbon atoms in a vicinity of the cathode having the biofilm in electrical communication therewith, and generating molecular oxygen at the anode.

In one embodiment of the method, the reaction vessel has a first chamber and a second chamber, the first chamber and the second chamber each configured to contain a working fluid having mobile ions therein, the first chamber and the second chamber separated by a membrane permeable to at least a selected ionic species, the anode electrode disposed in one of the first chamber and the second chamber and the cathode electrode disposed in the other of the first chamber and the second chamber.

In one embodiment of the method, the source of carbon dioxide is selected from among carbon dioxide in an effluent from a combustion process of coal, petroleum, methane, natural gas, biomass, organic carbon, an industrial process that releases carbon dioxide, carbon dioxide from geothermal sources, atmospheric CO2, $CO_2$ from dry ice, $CO_2$ from carbonate minerals, $CO_2$ from carbonic acid ($H_2CO_3$), and $CO_2$ sequestered from the atmosphere.

In one embodiment of the method, the biofilm mediates the production of the chemical containing at least two carbon atoms using a reverse tricarboxylic acid pathway.

BRIEF DESCRIPTION OF THE DRAWINGS

In FIG. 2A, Fe(II) production from the reduction of Fe(III) following the first transfer of a 1% inoculum from cultures grown with acetate as the electron donor and Fe(III) as the electron acceptor is shown. In FIG. 2B, Fe(II) production upon of a second transfer of a 2% inoculum of strain ACL from panel A into fresh medium is shown.

DETAILED DESCRIPTION

The discovery of electrotrophs, microorganisms that can directly accept electrons from electrodes for the reduction of terminal electron acceptors, has spurred the investigation of a wide range of potential applications. Potential electron acceptors include: carbon dioxide, nitrate, metals, chlorinated compounds, organic acids, protons and oxygen. Direct electron transfer from electrodes to cells has many advantages over indirect electrical stimulation of microbial metabolism via electron shuttles or hydrogen production. Supplying electrons with electrodes for the bioremediation of chlorinated compounds, nitrate or toxic metals may be preferable to adding organic electron donors or hydrogen to the subsurface or bioreactors.

The term "microbial electrosynthesis" refers to the reduction of carbon dioxide to multicarbon compounds with electrons donated from an electrode as the electron donor. Microbial electrosynthesis differs significantly from photosynthesis in that carbon and electron flow is directed primarily to the formation of extracellular products, rather than biomass. Biomass typically requires extensive additional processing for chemical or fuel production. Coupling photovoltaic technology with microbial electrosynthesis represents a novel photosynthesis strategy that avoids many of the drawbacks of biomass-based strategies for the production of transportation fuels and other organic chemicals.

Engineered microbial processes, such as the production of fuels and other chemicals as well as bioremediation, have traditionally relied on biomass-based organic feedstocks as the electron donor. Potential advantages of microbial electrosynthesis over biomass-based strategies for the production of fuels and chemicals include: the one-hundred-fold higher efficiency of photovolatics in harvesting solar energy; eliminating the need for arable land; avoiding the environmental degradation (such as introduction of excess nutrients and other pollutants) associated with intensive agriculture; and the direct production of desired products. Like photovolatics, other major renewable forms of energy such as wind, hydro and geothermal can also produce electricity. Therefore, the possibility of powering beneficial microbial processes with electricity is becoming increasingly attractive. As detailed below, this may be most effectively accomplished by providing microorganisms with electrons via direct electron transfer from electrodes, coupled to the microbial reduction of various electron acceptors.

Microorganisms capable of directly accepting electrons from electrodes have been referred to colloquially as electrode-oxidizing bacteria, just as microorganisms are referred to as iron-oxidizing, sulfur-oxidizing or methane-oxidizing microbes. A more formal designation may be electrotrophs in accordance with the standard parlance of chemotrophs that oxidize chemical compounds in their environments (organotrophs oxidize organic compounds; lithotrophs oxidize inorganics) and phototrophs.

The microbial production of organic compounds from water and carbon dioxide using electric currents is described in U.S. Pat. No. 9,175,408, which is incorporated in its entirely by reference herein.

As described herein, a newly constructed *Geobacter* strain has demonstrated the ability to achieve high current densities on cathodes with a microbial chassis that is amendable for the introduction of diverse synthetic metabolic pathways to produce fuels and organic commodities with renewable electricity as the primary energy source.

A genetically tractable microbial strain that can grow effectively on cathodes under anaerobic conditions has been constructed. *G. sulfurreducens* is known for its mechanisms for extracellular electron exchange and basic metabolism. On anodes, *G. sulfurreducens* produces the highest current densities of any pure culture, which has been attributed to its ability to produce electrically conductive biofilms that enable cells at distance from the anode to participate in biofilm-electrode electron exchange. There is debate over the mechanisms for long-range electron conduction through the biofilms, but it is clear that the conductivity of anode biofilms is sufficient to support long-range electron transport to support the respiration of cells not in contact with electrodes.

Cathode biofilms of wild-type *G. sulfurreducens* consume twenty-fold less current than the current densities they produce on anodes. In order to grow on cathodes, wild-type *G. sulfurreducens* requires acetate (1-2 mM) as a carbon source. However, the added acetate can also serve as an electron donor. It was hypothesized that the simultaneous supply of electrons from both acetate and the cathode might prevent cells from optimizing their metabolism for robust growth on cathodes.

In order to construct a strain of *G. sulfurreducens* that did not require an organic carbon source, an ATP-dependent citrate lyase was introduced to provide the one enzyme that *G. sulfurreducens* would require for a complete complement of enzymes necessary for a reverse TCA cycle (FIG. 1A, Table 1) that has the potential to make necessary biosynthetic precursors from carbon dioxide. The genes aclA and aclB, which encode the two subunits for the ATP-citrate lyase of *Chlorobium limicola*, were synthesized with codon optimization for *G. sulfurreducens*. These synthetic genes were introduced into the chromosome adjacent to the gene (GSU1106) for citrate synthase (FIG. 1B) with known methods. Expression of the introduced genes was induced by isopropyl β-D-1-thiogalactopyranoside (IPTG) at a concentration of 1 mM. This strain was designated *G. sulfurreducens* strain ACL (ATP-dependent citrate lyase).

TABLE 1

Figure 1A:
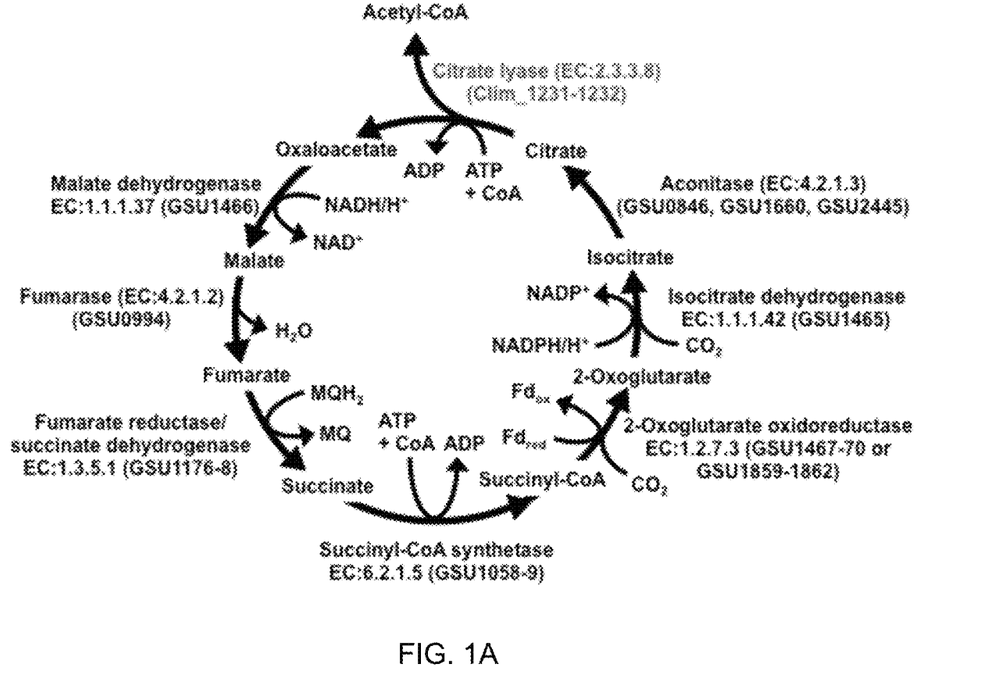
FIG. 1A depicts a reverse TCA cycle in *Geobacter sulfurreducens*. Genes for enzymes required for the TCA cycle present in the native *G. sulfurreducens* genome and the requirement for ATP-dependent citrate lyase to complete the pathway are shown.
Figure 1B:
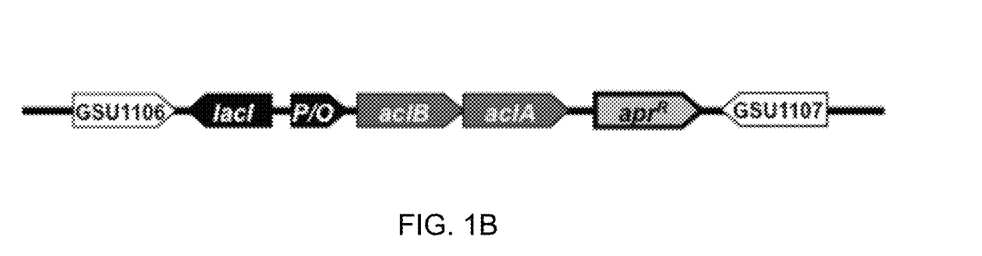
FIG. 1B depicts a gene arrangement to introduce genes for ATP-dependent citrate lyase. Citrate lyase genes: aclA and aclB; Lac repressor gene; lacI; tac-lac promoter/lac operator (IPTG-inducible): P/O; Apramycin resistance gene: $apr^R$ are included.

Enzymes and their gene numbers in the reverse TCA cycle.

| Enzyme | Category | Gene number |
|---|---|---|
| Citrate lyase | EC: 2.3.3.8 | Clim_1231-1232 |
| Aconitase | EC: 4.2.1.3 | GSU0846, GSU1660, GSU2445 |
| Isocitrate dehydrogenase | EC: 1.1.1.42 | GSU1465 |
| 2-Oxoglutatate oxidoreductase | EC: 1.2.7.3 | GSU1467-70 |
| Succinyl-CoA synthetase | EC: 6.2.1.5 | GSU1058-9 |
| Fumarate reductase/ succinate dehydrogenase | EC: 1.3.5.1 | GSU1176-8 |
| Fumarase | EC: 4.2.1.2 | GSU0994 |
| Malate dehydrogenase | EC: 1.1.1.37 | GSU1466 |

Figure 2A:
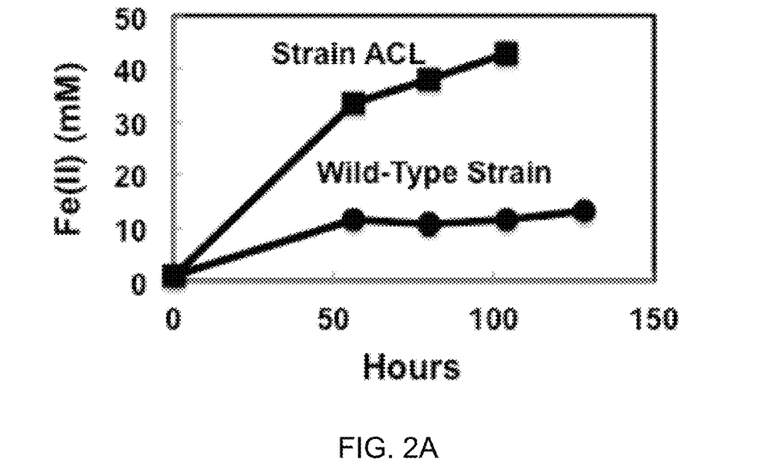
FIGS. 2A and 2B are graphs that show the autotrophic growth of strain ACL with $H_2$ as the electron donor and Fe(III) citrate as the electron acceptor.
Figure 2B:
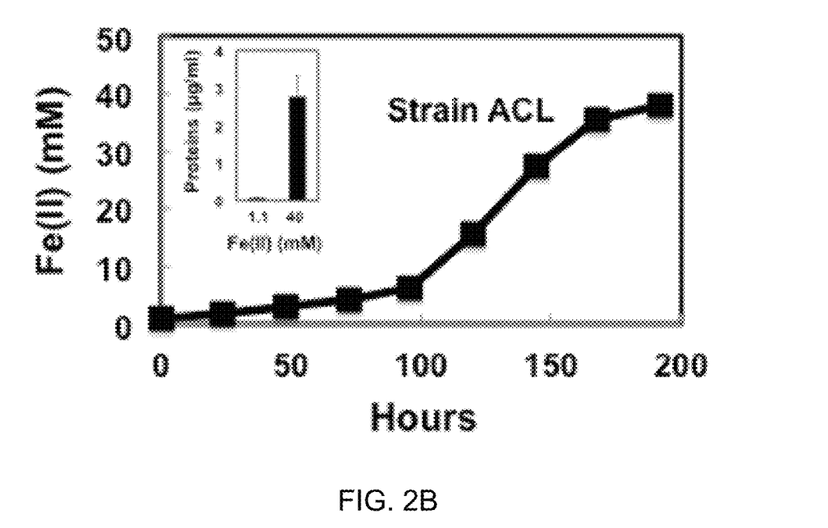
Figure 3A:
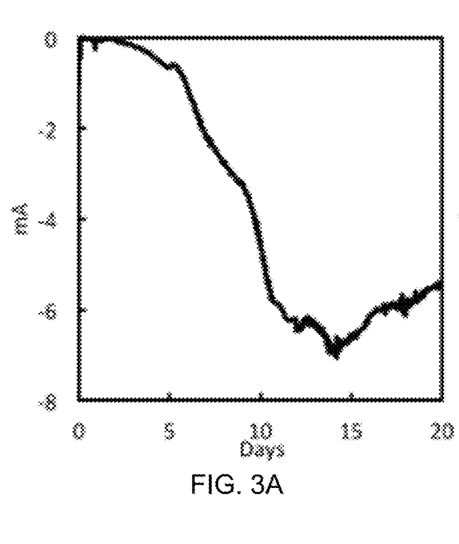
FIGS. 3A-3D are graphs that show the current consumption over time by strain ACL in four replicate bioelectrochemical devices. Cells were grown under anaerobic conditions with fumarate as electron acceptor in two-chambered systems with graphite electrodes with the graphite cathode poised at −500 mV versus Ag/AgCl.
Figure 3B:
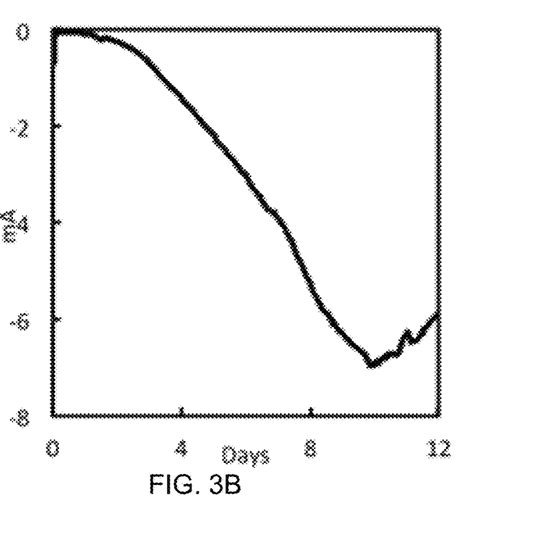
Figure 3C:
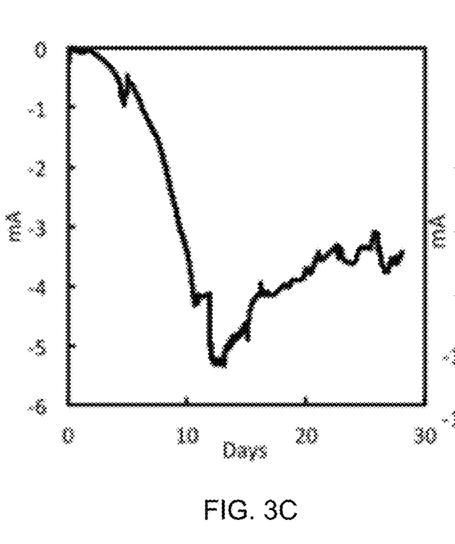
Figure 3D:
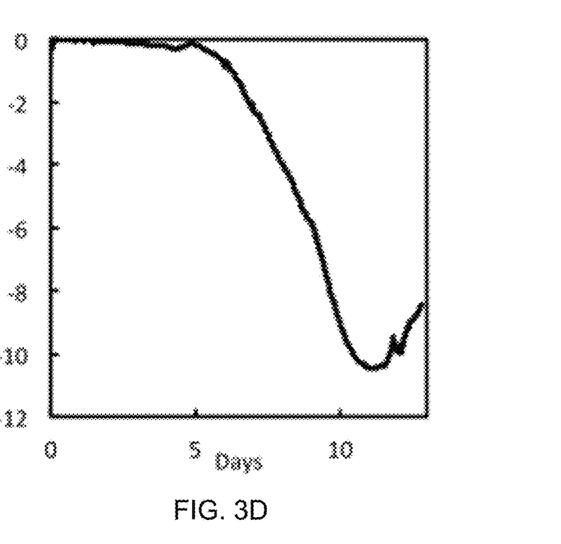

FIGS. 2A and 2B show autotrophic growth of the ACL strain with $H_2$ as the electron donor and Fe(III) citrate as the electron acceptor. In FIG. 2A, Fe(II) production from the reduction of Fe(III) following the first transfer of a 1% inoculum from cultures grown with acetate as the electron donor and Fe(III) as the electron acceptor is shown. In FIG. 2B, Fe(II) production upon of a second transfer of a 2% inoculum of strain ACL from panel A into fresh medium is shown. The inset in FIG. 2B shows the increase in protein concentration of strain ACL associated with Fe(III) reduction. The results are the means of duplicate cultures. To estimate cell growth, total cell extracts were prepared with B-PER Complete Bacterial Protein Extraction Reagent (Thermo Fisher Scientific) and the amount of protein was measured with the Bradford Protein Assay (Bio-Rad).

The wild-type strain of *G. sulfurreducens* could not sustain metabolism with $H_2$ as the electron donor and Fe(III) citrate as the electron acceptor in the absence of a carbon source (FIG. 2A). However, strain ACL grew in repeated transfers into Fe(III) citrate medium with $H_2$ as the electron donor and carbon dioxide as the sole carbon source (FIG. 2B). Fe(III) reduction was accompanied with an increase in cell protein (FIG. 2B inset). These results demonstrate that expression of the ATP-dependent citrate lyase was sufficient to confer the capacity for autotrophic growth.

Referring to FIGS. 3A to 3D, current consumption over time by strain ACL in four replicate bioelectrochemical devices is shown. Cells were grown under anaerobic conditions with fumarate as electron acceptor in two-chambered systems with graphite electrodes with the graphite cathode poised at −500 mV versus Ag/AgCl. On cathodes, strain ACL consistently consumed a maximum of more than 5 mA with fumarate as the electron acceptor. This is more than ten-fold the maximum current consumption of ≤0.5 mA typically observed with the wild-type strain.

Figure 4A:
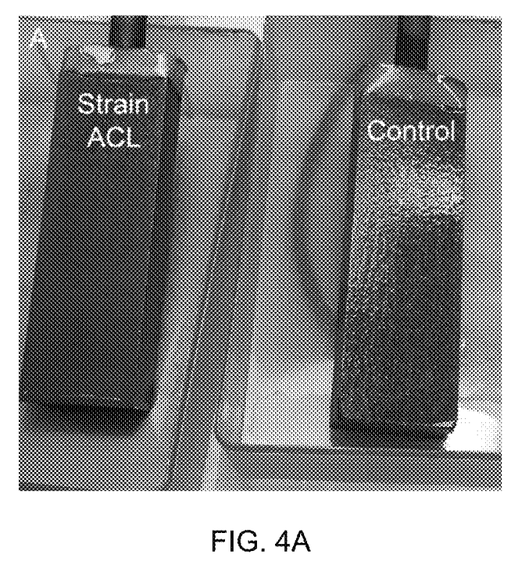
FIG. 4A is a photograph showing the appearance of cathode biofilms of ACL and control strains without citrate lyase genes.
Figure 4B:
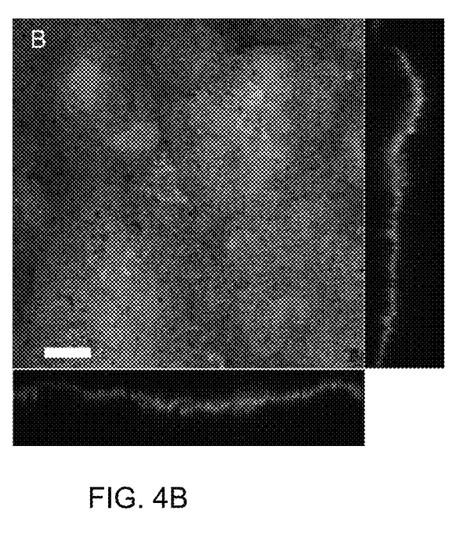
FIGS. 4B and 4C show confocal scanning laser micrographs of cathode biofilms of ACL (FIG. 4B) and wild type (FIG. 4C) strains treated with Live/Dead stain (Size bar=50 μm).
Figure 4C:
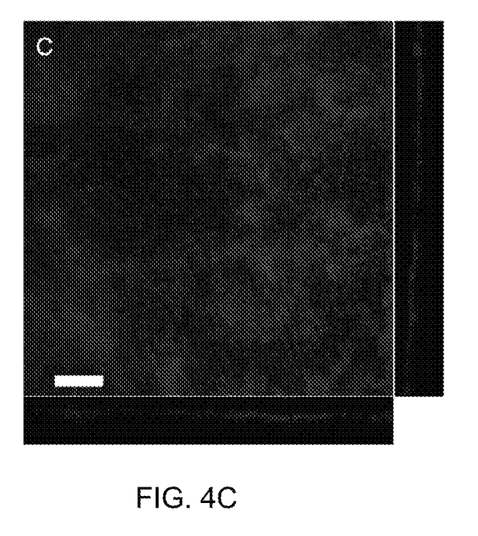

Referring to FIG. 4A, the appearance of cathode biofilms of ACL and control strains without citrate lyase genes are shown. The improved growth of strain ACL on the cathodes was visually apparent as thick, red biofilms. In contrast, wild-type cells produced cathode biofilms that were barely visible. In FIGS. 4B and 4C, confocal scanning laser microscopy images of the cathodes colonized by strain ACL revealed thick biofilms (ca. 35 μm) that predominantly stained green with Live/Dead stain, suggesting that cells were metabolically active with intact membranes (FIG. 4B). Wild-type cathode biofilms were thinner (<10 μm), very patchy, and stained predominately red, suggesting that many of the cells were moribund (FIG. 4C).

The stoichiometry of total current consumption by mature cathode biofilms of strain ACL, and the simultaneous recovery of electrons in the reduction of fumarate to succinate, was determined over six hour intervals in three separate bioelectrochemical devices. Coulombs of current consumed from the electrode and coulomb equivalents recovered in succinate production for the three replicate systems were: 40 coulombs consumed/41 recovered in succinate (recovery 102.5%); 103 coulombs consumed/96 recovered in succinate (recovery 93.2%); and 139 coulombs consumed/145 recovered in succinate (recovery 104.3%); yielding a mean and standard deviation of 100±6% for electron recovery in the triplicate studies.

Figure 5:
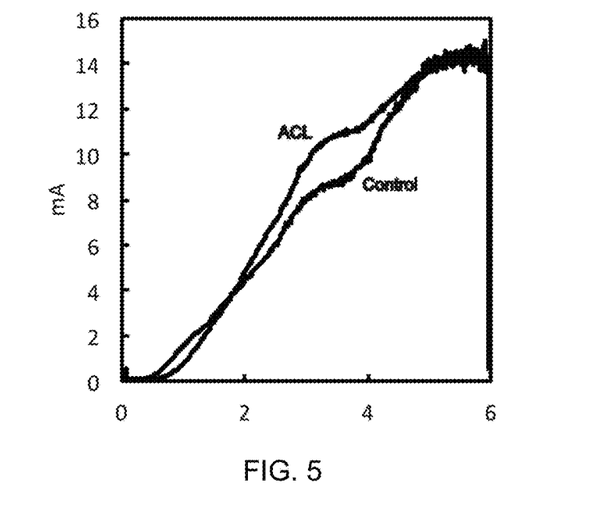
FIG. 5 is a graph that shows the representative current production of the ACL and wild-type strains over time with acetate as the electron donor. Cells were grown under anaerobic conditions in two-chambered systems with graphite electrodes with the graphite anode poised at +300 mV versus Ag/AgCl.

Referring to FIG. 5, representative current production of the ACL and wild-type strains over time with acetate as the electron donor are shown. Cells were grown under anaerobic conditions in two-chambered systems with graphite electrodes with the graphite anode poised at +300 mV versus Ag/AgCl. Strain ACL generated currents comparable to those previously reported for the wild-type strain under similar conditions. Carbon dioxide fixation by the reverse TCA cycle is not required during growth on acetate. Thus, possession of ATP-dependent citrate lyase would not be expected to enhance current production by strain ACL.

It is believed that strain ACL is the first microorganism shown to grow effectively under anaerobic conditions with electrons derived from a cathode as the sole electron donor. Surprisingly, strain ACL is capable of maximum rates of current consumption ($\geq 0.8$ A/m$^2$) that exceed the maximum current-consumption rates (ca. 0.04 A/m$^2$) of the intensively studied MCL aerobic cathode biofilms, even though oxygen is an energetically more favorable electron acceptor than fumarate. In accordance with its higher current consumption capabilities, strain ACL cathode biofilms are much thicker than the $\leq 10$ μm MCL cathode biofilms. The simple pure culture composition of the strain ACL cathode biofilm and the possibility of querying the function of specific proteins with genetic manipulation make strain ACL an effective model organism for investigations on the mechanisms by which microorganisms can successfully function on cathodes.

Although cathode-driven processes such as microbial electrosynthesis and electrofermentations to produce simple organic acids and alcohols can be carried out with enriched mixed microbial communities, the production of more complex, high value chemicals is likely to require synthetic biology to introduce novel metabolic pathways. Strain ACL may be the ideal chassis for such endeavors. Not only can strain ACL effectively grow on cathodes, but a detailed genome-scale metabolic model and substantial genetic tools are already available to aid in strain design. Strain ACL provides a major step forward in the design of cathode-based bioelectrochemical technologies.

Engineering Strain ACL to Produce Ethanol

Figure 6A:
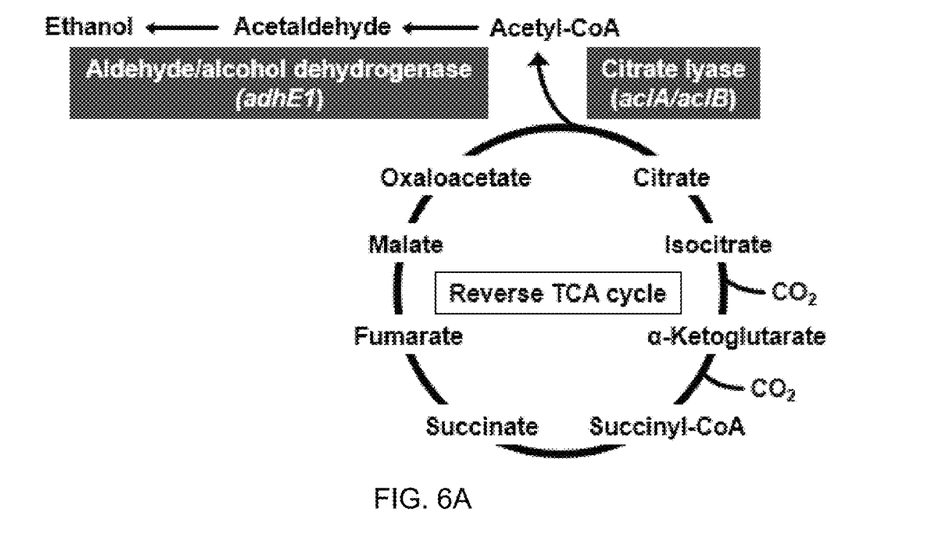
FIG. 6A depicts a reverse TCA cycle in *Geobacter sulfurreducens*. The adhE1 gene is responsible for ethanol production from acetyl-CoA via acetaldehyde.
Figure 6B:
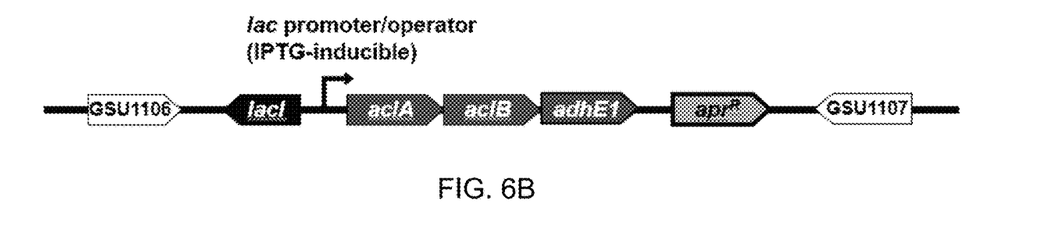
FIG. 6B depicts a gene arrangement to produce ethanol from carbon dioxide with the ACL strain. The arrangement includes: Citrate lyase genes: aclA and aclB; adhE1 gene for bifunctional aldehyde/alcohol dehydrogenase; Lac repressor gene; lacI; lac promoter/lac operator (IPTG-inducible); Apramycin resistance gene: $apr^R$.

Referring to FIGS. 6A and 6B, the aclA/aclB genes together with the adhE1 gene were introduced in the chromosome of *Geobacter sulfurreducens*. The aclA/aclB/adhE1 genes are in an operon (same transcription unit) under the control of the lac promoter/operator (IPTG-inducible). The adhE1 gene originated from *Clostridium ljungdahlii*, which encodes bifunctional aldehyde/alcohol dehydrogenase and was shown to be responsible for ethanol production from acetyl-CoA via acetaldehyde, was optimized for codon usages in *G. sulfurreducens*. This strain produced ethanol (100 μm) from carbon dioxide when grown with hydrogen as the electron donor and Fe(III) as the electron acceptor.

While the disclosed invention has been explained in relation to various detailed embodiments, it is to be understood that various modifications thereof may become apparent to those skilled in the art upon reading the specification. Therefore, it is to be understood that the invention specified herein is intended to include such modifications as may fall within the scope of the appended claims.

The invention claimed is:

1. A genetically engineered *Geobacter sulfurreducens* strain, wherein the strain comprises a genetically engineered modification resulting from the insertion of a genetic element encoding ATP-citrate lyase (EC 2.3.3.8), wherein the strain is capable of effectively growing on a cathode under anaerobic conditions with electrons derived solely from the cathode as electron donor source.

2. The genetically engineered *Geobacter sulfurreducens* strain of claim 1, wherein the genetic element comprises the genes aclA and aclB.

3. The genetically engineered *Geobacter sulfurreducens* strain of claim 1, wherein the genetic element is inserted adjacent the gene GSU1106 of the parent *Geobacter sulfurreducens*.

4. The genetically engineered *Geobacter sulfurreducens* strain of claim 1, wherein the genetically engineered modification further comprises the insertion of a gene that encodes bifunctional aldehyde/alcohol dehydrogenase.

5. The genetically engineered *Geobacter sulfurreducens* strain of claim 4, wherein the gene encoding bifunctional aldehyde/alcohol dehydrogenase is adhE1.

6. The genetically engineered *Geobacter sulfurreducens* strain of claim 1, wherein the genetically engineered *Geobacter sulfurreducens* strain is configured for producing a carbonaceous chemical containing at least two carbon atoms in a reverse tricarboxylic acid (TCA) pathway.

7. The genetically engineered *Geobacter sulfurreducens* strain of claim 1, wherein the strain is identified as strain ACL.

8. The genetically engineered *Geobacter sulfurreducens* strain of claim 1, wherein the genetically engineered *Geobacter sulfurreducens* strain exhibits improved function as a cathode biofilm compared to the wild-type *Geobacter sulfurreducens* under the same conditions.

9. A method of generating a carbonaceous chemical wherein carbon dioxide is a source of carbon, comprising the steps of:

providing a reaction vessel having an anode electrode and a cathode electrode disposed therein, said anode electrode having at least one surface and an anode electrical contact terminal, said cathode electrode having at least one surface and a cathode electrical contact terminal, said cathode electrode having a film of biologically active material comprising the genetically engineered *Geobacter sulfurreducens* strain of claim 1 adjacent said at least one surface of said cathode electrode and in electrical communication therewith, said reaction vessel configured to contain a working fluid having mobile ions therein;

providing a reaction medium in contact with said cathode electrode and said anode electrode, said reaction medium containing a substance configured to be oxidized;

providing a source of electrical energy electrically connected to said cathode electrical contact terminal and to said anode electrical contact terminal;

providing a source of carbon dioxide configured to provide carbon dioxide to said film of biologically active material adjacent said at least one surface of said cathode electrode by way of said reaction medium;

operating said source of electrical power to provide electrons to said cathode and to extract electrons from said anode; and generating a carbonaceous chemical containing at least two carbon atoms in a vicinity of said cathode having said biofilm in electrical communication therewith, and generating molecular oxygen at said anode.

10. The method of claim 9, wherein said reaction vessel has a first chamber and a second chamber, said first chamber and said second chamber each configured to contain a working fluid having mobile ions therein, said first chamber and said second chamber separated by a membrane permeable to at least a selected ionic species, said anode electrode disposed in one of said first chamber and said second chamber and said cathode electrode disposed in the other of said first chamber and said second chamber.

11. The method of claim 9, wherein said source of carbon dioxide is selected from the group consisting of carbon dioxide in an effluent from a combustion process of coal, petroleum, methane, natural gas, biomass, organic carbon, an industrial process that releases carbon dioxide, carbon dioxide from geothermal sources, atmospheric CO2, $CO_2$ from dry ice, $CO_2$ from carbonate minerals, $CO_2$ from carbonic acid ($H_2CO_3$), and $CO_2$ sequestered from the atmosphere.

12. The method of claim 9, wherein said biofilm mediates said production of said chemical containing at least two carbon atoms using a reverse tricarboxylic acid pathway.

* * * * *